United States Patent [19]

Cottrell

[11] Patent Number: 5,352,848
[45] Date of Patent: Oct. 4, 1994

[54] NITRILE REMOVAL IN AN ETHERIFICATION PROCESS

[75] Inventor: Paul R. Cottrell, Arlington Heights, Ill.

[73] Assignee: UOP, Des Plaines, Ill.

[21] Appl. No.: 997,830

[22] Filed: Dec. 29, 1992

[51] Int. Cl.$^5$ .............................. C07C 41/04
[52] U.S. Cl. .................... 568/699; 568/697; 585/800; 585/802; 203/29; 203/DIG. 6
[58] Field of Search ........... 568/697, 699; 585/802, 585/800; 203/29, DIG. 6

[56] References Cited

U.S. PATENT DOCUMENTS

| | | | |
|---|---|---|---|
| 4,831,206 | 5/1989 | Zarchy | 585/737 |
| 5,120,881 | 6/1992 | Rosenfeld et al. | 568/697 |
| 5,166,454 | 11/1992 | Harandi et al. | 568/697 |
| 5,238,541 | 8/1993 | Marquez et al. | 203/56 |

FOREIGN PATENT DOCUMENTS 0118531  7/1983  Japan ................. 568/697

*Primary Examiner*—Johann Richter
*Assistant Examiner*—Michael B. Hydorn
*Attorney, Agent, or Firm*—Thomas K. McBride; John F. Spears, Jr.; Reginald K. Taylor

[57] ABSTRACT

In an etherification process that uses an FCC effluent as a source of isoolefins, the buildup of nitriles in an alcohol-containing stream that is recycled to the etherification zone is prevented by dragging at least a portion of the methanol-containing stream to the FCC reaction zone. As a result, the etherification catalyst deactivation rate is reduced.

20 Claims, 1 Drawing Sheet

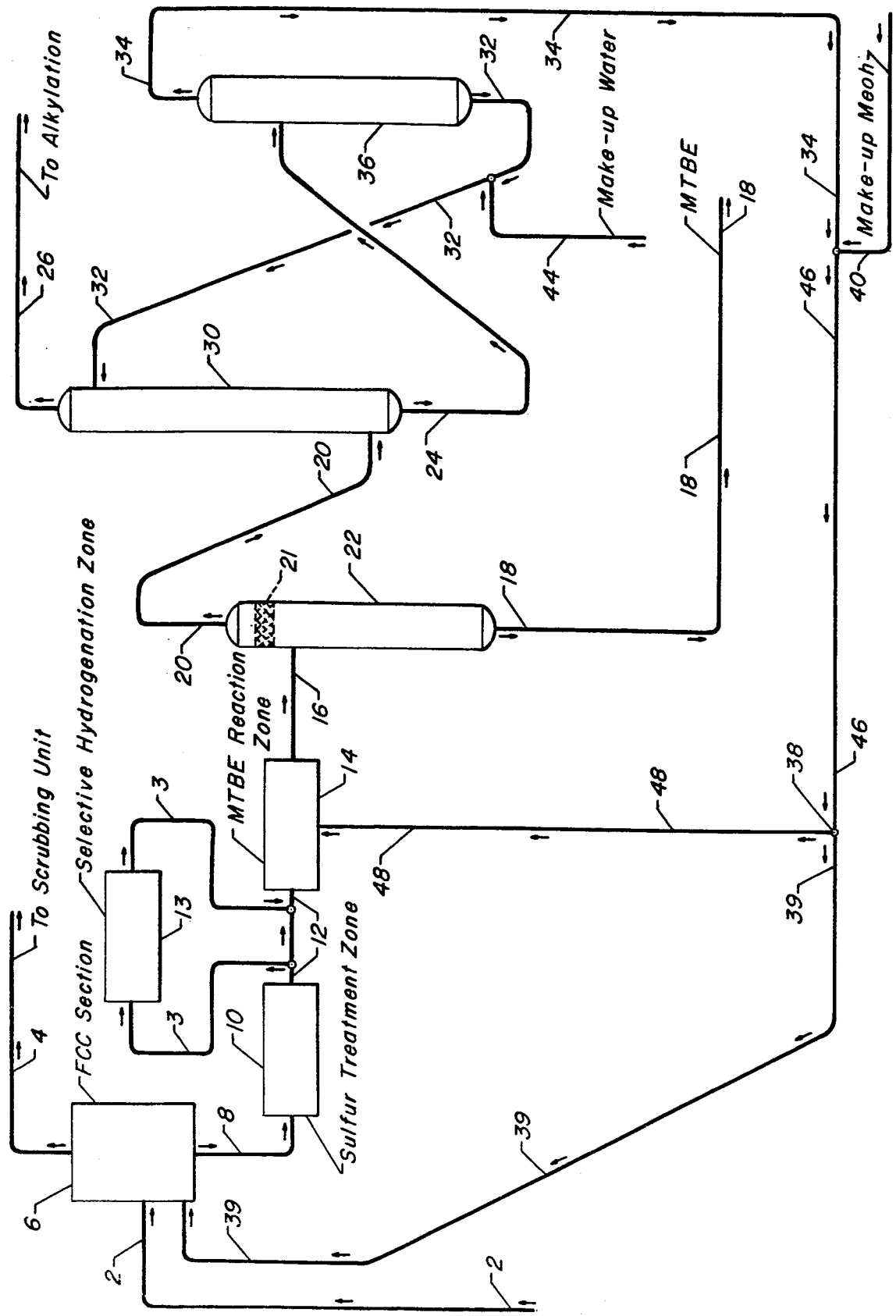

NITRILE REMOVAL IN AN ETHERIFICATION PROCESS

FIELD OF THE INVENTION

This invention relates to a method of removing nitriles from a fluid catalytic cracking (FCC) effluent prior to contacting the FCC effluent with an alcohol in an etherification zone.

BACKGROUND OF THE INVENTION

Oxygenates, such as ethers, have been a part of the U.S. gasoline strategy since the late 1970's. These materials reduce carbon monoxide emissions and unburned hydrocarbons in the exhaust of internal combustion engines. Another advantage of oxygenates is that they have relatively good blending characteristics. Some oxygenates have better blending characteristics than others. For example, the blending vapor pressures of methyl tertiary butyl ether (MTBE), ethyl tertiary butyl ether (ETBE), and tertiary amyl ether (TAME) are lower than methanol and ethanol, making them more attractive gasoline components.

MTBE or TAME can be produced by the addition of methanol to the corresponding isoolefin under etherification conditions. The reaction takes place in the presence of a catalyst at mild operating temperatures and pressures. The catalyst is usually a macrorecticular ion exchange resin based on a sulfonate styrene divinylbenzene copolymer.

It is not unusual for side reactions to occur during etherification reaction. For example, typical side reactions that can occur in an MTBE reactor include: (1) the formation of tertiary butyl alcohol (TBA) by isobutylene hydration; (2) the formation of di-isobutylene (DIB) by isobutylene dimerization; and the formation of dimethyl ether (DME) and water by methanol dehydration.

Downstream processing of the methyl tertiary butyl ether effluent usually includes separation of the ether products from the unconverted reactants, e.g., methanol. Effluent from the etherification reactor is usually passed to a fractionation tower where the methyl tertiary butyl ether product is removed from the bottom while side reaction products and unreacted reactants are separated as a raffinate overhead stream. The methanol contained in the raffinate is extracted with water by countercurrent, liquid-liquid extraction in a raffinate water wash tower. A methanol-containing stream leaves the bottom of the raffinate water wash tower and enters a methanol-water fractionation tower. A methanol-free raffinate stream leaves the top of the water wash tower and is directed to further downstream processing, e.g., alkylation. A water-containing stream free of methanol exits the bottom of the fractionation tower and is recycled for reuse in the raffinate water wash tower. A methanol-rich stream leaves the top of the fractionation tower and is recycled to the etherification reactor.

The most common source of isoolefinic hydrocarbons for use as a feedstock in an etherification process is the effluent from a fluid catalytic cracking (FCC) unit. FCC is a process for the conversion of straight-run atmospheric gas oil, vacuum gas oil, certain atmospheric residues, and heavy stocks recovered from other operations into high octane gasoline, light fuel oils and olefin-rich light gases. In simplified terms, the cracking reactions are carried out in a vertical reactor vessel in which vaporized oil rises and carries along with it, in intimate contact, small fluidized catalyst particles. The reactions are very rapid, and only a few seconds of contact time are necessary for most applications. In a petroleum refinery, the FCC unit typically processes 30–50% of the crude oil charged to the refinery.

Early FCC units were designed to operate on vacuum gas oils directly fractionated from crude oils. Typically, these vacuum oils came from high quality crude oils. Today, much of the high quality feedstock for FCC units have been depleted and modern FCC units process less favorable materials. These less favorable materials include a substantial amount of sulfur compounds, metal cations, and nitrogen compounds. As a result, the contaminant levels in the FCC effluent have been growing, particularly in the $C_3$–$C_5$ effluent fraction. Without appropriate treatment, the contaminants in the $C_3$–$C_5$ FCC effluent fraction can be transmitted to sensitive downstream processes where they reduce the effectiveness of downstream catalysts and create unfavorable by-product reactions in processes such as etherification.

The use of FCC effluent as a feedstock for an etherification process can pose problems due to the above-described impurities. The FCC effluent stream usually contains a significant amount of metal cations that can deactivate the etherification ion exchange resin catalyst by plug flow neutralization. Plug flow neutralization occurs when a strong cation such as sodium reacts with sulfonic acid groups on the catalyst. This type of neutralization begins at the reactor inlet bed and slowly moves along the length of the reactor over a period of time. The FCC effluent will also contain some nitrogen compounds, such as ammonia, light amines, dimethylformamide, and N-methyl-pyrrolidine.

SUMMARY OF THE INVENTION

Of particular concern to those who use FCC effluent as an olefinic feedstock for an etherification process are the presence of nitriles having 1 to 3 carbon atoms, in particular propionitrile and acetonitrile (ACN). In particular, there is a concern about the buildup of nitriles in the alcohol stream that is recycled back to the etherification reactor. The buildup of nitriles on the etherification catalyst will be a flat profile across the catalyst bed. In other words, unlike the basic nitrogenates such as ammonia, the resin does not remove nitriles in a plug flow manner. As a result, in the case of nitrile contamination, the etherification catalyst continuously deactivates itself.

In the past, nitrogen compounds contained in FCC effluents bound for downstream hydrocarbon conversion processes were removed using complicated and expensive pretreatment systems, e.g., once through water wash or nitrogen removal units. The once through water wash approach uses a countercurrent liquid-liquid tower wherein the FCC effluent is contacted with a high quality water-containing stream. Although from an equilibrium point of view the water wash should effectively remove the nitriles, the cost of the water wash system, which includes a large fractionation tower, can be prohibitive.

A nitrogen removal unit (NRU) usually consists of a group of regenerable beds that adsorb the nitriles and other nitrogen components from the FCC effluent. The beds would be regenerated by an available regenerant determined for each unit. This regenerant can represent a problem in itself. The nitrogen components will be buried in the regenerant and must be removed or blended with another stream. If the regenerant is to be scrubbed, the cost of the materials and utilities required could be prohibitive. Blending the regenerant with gasoline could cause the blended gasoline product to develop color bodies or make the blended gasoline unstable.

The present invention solves the above-described nitrile build-up problem by dragging at least a portion of the alcohol recycle stream to the FCC reaction zone where the nitriles are neutralized. Although not wanting to be limited by theory, it is believed that the nitriles react with water present in an FCC reaction zone to form ammonia that can be readily separated from the FCC effluent. Consequently, the aforementioned buildup of nitriles in the alcohol-containing stream that is recycled to the etherification zone does not occur. Therefore, the deactivation rate of the etherification catalyst is decreased without incurring the sizeable capital outlay required for the previously-mentioned pretreatment systems.

The present invention is a method of treating an effluent of a fluid catalytic cracking zone, the effluent comprising at least one nitrile compound which method comprises the steps of: contacting the effluent with a $C_1$-$C_5$ monohydroxy alcohol in the presence of an etherification catalyst in an etherification zone under etherification conditions to react the isoalkenes with the alcohol to produce an etherification effluent stream; passing at least a portion of the etherification effluent stream to a separation zone to produce an ether-rich stream and a raffinate stream comprising the nitrile; passing the raffinate stream to an alcohol recovery zone to produce a hydrocarbon-rich raffinate stream and an alcohol-containing stream; and recycling at least a portion of the alcohol-containing stream to the fluid catalytic cracking zone.

In one embodiment, the present invention is a method of treating an effluent of a fluid catalytic cracking zone, the effluent comprising at least one nitrile compound which method comprises the steps of: contacting the effluent with methanol in the presence of an etherification catalyst in an etherification zone under etherification conditions to react the isobutene with the methanol to produce an etherification effluent stream which comprises methyl tertiary butyl ether; passing at least a portion of the etherification effluent stream to a distillation zone and contacting the methanol in the bed of catalyst at etherification conditions to produce a methyl tertiary butyl ether-rich stream and an overhead raffinate stream; contacting the raffinate stream with a water-containing stream to produce a hydrocarbon-rich raffinate stream and a methanol-containing stream; monitoring nitrile concentration of the methanol-containing stream; and regulating the nitrile concentration in the methanol-containing stream by recycling at least a portion of the methanol-containing stream to the fluid catalytic cracking zone.

In another embodiment, the present invention is a method for fluid catalytic cracking of a hydrocarbon feedstock which method comprises the steps of: contacting the hydrocarbon feedstock with a fluid catalytic cracking catalyst in a fluid catalytic cracking zone under fluid catalytic cracking conditions to produce a fluid catalytic cracking effluent; treating the fluid catalytic cracking effluent stream to remove a substantial amount of any sulfur compounds contained therein; contacting the effluent with a selective hydrogenation catalyst at selective hydrogenation conditions in a selective hydrogenation zone to selectively saturate diolefins to monoolefins; contacting the effluent with methanol in the presence of an etherification catalyst comprising a macroporous acid-form sulfonic ion exchange resin in an etherification zone under etherification conditions to react the isobutene with the methanol to produce an etherification effluent stream which comprises methyl tertiary butyl ether; passing at least a portion of the etherification effluent stream to a distillation zone containing a bed of etherification catalyst comprising a macroporous acid-form sulfonic ion exchange resin and contacting the methanol in the bed of catalyst at etherification conditions to produce a methyl tertiary butyl ether-rich stream and an overhead raffinate stream comprising isobutane, normal butene, and normal butane isomers, and unconverted methanol and isobutene; contacting the raffinate stream with a water-containing stream to produce a hydrocarbon-rich raffinate stream and a methanol-containing stream; fractionating the methanol-containing stream to produce a methanol-rich stream; monitoring acetonitrile concentration of the methanol-rich stream; and regulating the acetonitrile concentration in the methanol-rich stream by recycling at least a portion of the methanol-rich stream to the fluid catalytic cracking zone.

DESCRIPTION OF THE DRAWING

The FIGURE is a schematic drawing of one embodiment of the present invention.

DESCRIPTION OF THE PREFERRED EMBODIMENT

The hydrocarbon feed stream of the present invention is an effluent from an FCC process. A typical feedstream will consist of a mixture of isobutane, isobutene, normal butane, 1-butene and 2-butene, 3-methyl-1butene, isopentane, 1-pentene, 2-methyl-1-butene, normal pentane, trans-2-pentene, cis-2-pentene and 2-methyl-2butene in a typical distribution of isomers.

Often the FCC effluent will contain diolefins in addition to the desired monoolefin feed components. These diolefins interfere with the operation of the catalyst in downstream processes by polymerizing and forming heavy hydrocarbons that block the active sites of the catalyst and prevent their use. In a preferred embodiment, the FCC effluent can undergo treatment for the elimination of diolefins. A common method of eliminating diolefins is by the selective hydrogenation of the olefins to saturate the diolefins into monoolefins. A particular catalyst and operating conditions for such selective dehydrogenation process can be found in U.S. Pat. Nos. 4,695,560 and 4,734,540, the contents of which are hereby incorporated by reference.

The selective hydrogenation process typically employs a nickel on aluminum catalyst or a noble metal, such as palladium on alumina, for selective hydrogenation. The nickel may be sulfided or unsulfided. The process can also operate in a broad range of operating conditions including pressures of from about 40–800 psig with pressures of between 50–300 psig being preferred and temperatures of from about 70°–700° F. with temperatures of from about 120°–400° F. being preferred. Effective space velocities for the processes should be above 1 hr$^{-1}$ and preferably above 5 with a range of from about 5 to 35 hrs$^{-1}$. It is typical in such a process to limit the amount of hydrogen to prevent the saturation of monoolefins such that there is less than twice the stoichiometric amount of hydrogen required for the selective hydrogenation in the process. Preferably, the mole ratio of hydrogen to diolefinic hydrocarbons in the material will be in the range of from 1:1 to 1.8:1, and in some cases the hydrogen will be less than the stoichiometrically required amount of hydrogen.

The hydrocarbon feedstock of the present invention may also contain a variety of sulfur compounds. Generally, the feedstream contains about 1 to 5000 ppm by weight $H_2S$ and COS, more typically from about 1–1000 ppm by weight $H_2S$, calculated as elemental sulfur of the feedstock.

In one embodiment of the present invention, the hydrocarbon feedstock of the present invention is passed into an amine treating zone for $H_2S$ and COS removal. This amine treating zone employs alkanolamines selected from the group consisting of monoethanolamine (MEA), diethanolamine (DEA), methyldiethanolamine (MDEA), and mixtures thereof. The amine treating zone is operated over a temperature ranging from about 60°–150° F. and a pressure ranging from about 15–500 psia. The amine treating will provide an $H_2S$- and COS-depleted stream which has been reduced by about 90% and preferably reduced by about 95% of the $H_2S$ and COS originally in the hydrocarbon feedstream.

In a preferred embodiment, the hydrocarbon feedstock of the present invention is passed to a mercaptan treating zone after amine treatment. In the mercaptan treating zone, the $H_2S$- and COS-depleted hydrocarbon feedstock is contacted with an alkaline scrubbing solution under mercaptan absorption conditions effective to produce a mercaptan-depleted stream and a mercaptide-containing scrubbing solution. The alkaline scrubbing solution may be selected from the group consisting of aqueous sodium hydroxide or aqueous ammonium hydroxide. The mercaptide-containing scrubbing solution is contacted with air or oxygen in the presence of an oxidation catalyst effective to regenerate the mercaptide-containing scrubbing solution. The temperature of the scrubbing solution ranges between about 10 and about 80° C. preferably about 20° C. and a pressure generally in the range of about 100 kPa absolute to about 3450 kPa absolute in order to keep the $H_2S$ and COS depleted stream in the liquid phase.

Additional information on the preferred mercaptan treating zone of the present invention can be found in U.S. Pat. Nos. 4,908,122 and 4,913,802 which are hereby incorporated by reference.

The hydrocarbon feedstream of the present invention will also contain nitrogen compounds, including ammonia, light amines, dimethylformamide, N-methylpyrrolidine, and nitriles having 1 to 3 carbon atoms, e.g., acetonitrile (ACN) and propionitrile. It is the reduction of these nitrile compounds to which the present invention is directed, in particular ACN.

The feed to the process of the present invention includes an alcohol to react with the isoolefin and produce the desired ether product. The alcohols that can be used are typically $C_1$–$C_5$ monohydroxy alcohols. Methanol typically constitutes the alcohol of choice. Ethanol is also an alcohol that is suitable for use in the present invention.

In accordance with the present invention, the hydrocarbon feedstock of the present invention is passed to an etherification zone along with alcohol in the presence of a catalyst under etherification conditions. For the sake of simplicity, hereinafter the etherification process will be described in terms of MTBE, however, the etherification process of the present invention also includes the production of TAME and ETBE.

The isobutylene, as well as the normal butene, will enter the etherification zone along with methanol. Contact with an etherification catalyst at etherification conditions will produce the MTBE product. A wide range of materials are known to be effective as etherification catalysts for the MTBE reaction including mineral acids such as sulfuric acid, boron trifluoride, phosphoric acid on kieselguhr, phosphorous-modified zeolites, heteropoly acids, and various sulfonated resins. The use of a sulfonated solid resin catalyst is preferred. These resin-type catalysts include the reaction products of phenolformaldehyde resins and sulfuric acid and sulfonated polystyrene resins including those crosslinked with divinylbenzene. A particularly preferred MTBE catalyst is a macroporous acid-form of a sulfonic ion exchange resin such as a sulfonated styrene-divinylbenzene resin as described in U.S. Pat. No. 2,922,822 having a degree of crosslinking of about 5 to 60%. Suitable resins are available commercially. Specialized resins have been described in the art and include copolymers of sulfonyl fluorovinyl ether and fluorocarbons as described in U.S. Pat. No. 3,489,243. Another specially prepared resin consists of the $SiO_2$-modified cation exchangers described in U.S. Pat. No. 4,751,343. The macroporous structure of a suitable resin is described in detail in U.S. Pat. No. 5,012,031 as having a surface area of at least about 400 $m^2/g$, a pore volume of about 0.6–2.5 ml/g and a mean pore diameter of 40–1000 Angstroms. It is contemplated that the subject process could be performed using a metal-containing resin which contains one or more metals from subgroups VI, VII or VIII of the Periodic Table such as chromium, tungsten, palladium, nickel, chromium, platinum, or iron as described in U.S. Pat. No. 4,330,679. Further information on suitable etherification catalysts may be obtained by reference to U.S. Pat. Nos. 2,480,940, 2,922,822, and 4,270,929.

A wide range of operating conditions are employed in processes for producing MTBE from isobutylene and methanol. Many of these include vapor, liquid, or mixed-phase operations. Processes operating with vapor or mixed phase conditions may be suitably employed in this invention. In a preferred embodiment, liquid phase conditions are used.

The range of etherification conditions for processes operating in liquid phase still includes a broad range of suitable conditions including a superatmospheric pressure sufficient to maintain the reactants as liquid phase, generally below about 700 psig, and a temperature between about 85° F. and about 210° F. Even in the presence of additional light materials, pressures in the range of about 140 to 580 psig are sufficient. A preferred temperature range is about 100°–210° F. The reaction rate is normally faster at higher temperatures, but conversion is more complete at lower temperatures due to favorable thermodynamics equilibrium. High conversion in a moderate volume reaction zone can, therefore, be obtained if the initial section of the MTBE reaction zone, e.g., the first two thirds, is maintained above 160° F. and the remainder of the MTBE reaction zone is maintained below 120° F. This may be accomplished most easily with two reactors. The ratio of methanol to isobutylene should normally be maintained in the range of about 1:1 to 2:1, preferably 1.05:1 and 1.5:1. An excess of methanol, above that required to achieve satisfactory conversion at good selectivity, should be avoided as some decomposition of methanol to dimethyl ether (DME) may occur which may increase the load on downstream separation facilities.

The MTBE reaction zone reacts selectively to principally convert only the isobutylene, therefore, butane and normal butene pass through the MTBE reaction zone without any significant conversion to products or by-products. Thus, the MTBE reaction zone effluent together with the unreacted isobutylene and methanol provide a stream of ether product and normal and branched butenes and butane isomers for separation.

The MTBE effluent exits the MTBE reaction zone and enters a separation zone. The separation zone can be any means known to those skilled in the art for separating a hydrocarbon stream into its various fractions. In a preferred embodiment, the arrangement of the separation zone consists of at least one distillation zone. In this distillation zone, a low boiling fraction comprising isobutane and methanol can be removed from the overhead stream of the distillation zone. In addition, the overhead stream can contain normal butene that was not reacted in the MTBE reaction zone and normal butane that entered the MTBE reaction zone as part of the hydrocarbon feedstream of the present invention. A high boiling fraction that principally comprises the MTBE product can be removed from the bottom portion of the distillation zone.

A useful arrangement for the separation zone of this invention is the use of a reactive distillation zone that contains a bed of etherification catalyst. The distillation zone can provide additional etherification of unreacted isobutene. Accordingly, the reactive distillation zone can be used as a combined reactor. Processes for the production of MTBE by reactive distillation are taught in U.S. Pat. Nos. 3,634,535 and 4,950,803. The operating conditions employed in the reactive distillation zone are generally the same as those outlined herein for the MTBE reaction zone. No particular apparatus or arrangement is needed to retain the catalyst bed within the distillation section of the reactive distillation zone and a variety of methods can be used to incorporate the bed or region of catalyst within the reactive distillation zone. For example, catalyst may be retained between suitable packing materials or may be incorporated onto a distillation tray itself. A preferred method of retaining the catalyst is through the use of a corrugated structural device that is described in U.S. Pat. No. 5,073,236 which is hereby incorporated by reference.

The MTBE product exits the bottom of the reactive distillation zone and is recovered. The overhead raffinate stream from the reactive distillation zone, comprising isobutane, normal butane, straight-chained butylene, a small amount of unreacted isobutylene, a small amount of unreacted methanol, DME, and TBA, is passed to a methanol recovery section.

The methanol recovery section may consist of a raffinate water wash zone and a methanol-water fractionation zone. In the raffinate water wash zone a water-containing stream enters the top of the zone and countercurrently contacts the overhead raffinate stream to remove methanol. Suitable operating conditions for the water wash zone include a temperature of about 100° F., a pressure of about 100 psi, and a water to methanol ratio of about 6 to 1. A hydrocarbon-rich raffinate stream having a methanol concentration of about 14 wt.% exits the raffinate water wash zone. This hydrocarbon-rich raffinate stream can be sent for further hydrocarbon processing, e.g., alkylation. A methanol-containing stream exits the bottom of the raffinate water wash zone.

As previously stated, it has been discovered that when an FCC effluent is used as a $C_4$ feedstock for the MTBE process a substantial amount of nitriles will build up over time in the methanol-containing stream that is recycled to the MTBE reaction zone. Left unchecked, the nitrile concentration in the methanol-containing stream can multiply to 100 times the concentration of nitrile entering the MTBE reactor in the FCC effluent. Accordingly, an essential feature of the present invention is dragging at least a portion of a methanol-containing stream to the FCC reaction zone so as to reduce the amount of ACN that is recycled to the MTBE reaction zone while using the methanol as a feed water replacement.

The exact portion of the methanol-containing stream that is passed to the FCC reaction zone will depend on the amount of nitrile that is entering the MTBE reaction zone through the FCC effluent. In one embodiment, the amount of the methanol-containing stream that is routed to the FCC reaction zone is that amount that is required to establish an equilibrium with the nitrile concentration that is entering the MTBE reaction zone in the FCC effluent. In a preferred embodiment, at least 50 mole % of the methanol-containing stream is recycled to FCC unit, preferably, at least about 75 mole %, most preferably at least about 85–100 mole %. In order to maintain steady state operating conditions in the MTBE reaction zone, whatever portion of the methanol-containing stream that is passed to the FCC reaction zone is made up by fresh makeup methanol. In a preferred embodiment, the methanol-containing stream has a nitrile concentration build-up concentration of less than about 1000 ppm, preferably less than about 100 ppm, most preferably less than about 50 ppm (all by weight).

In one embodiment of the present invention, the nitrile concentration in the methanol-containing stream is monitored, either intermittently or continuously. Based on the results of such monitoring, the nitrile concentration in the methanol-containing stream is then regulated by dragging that portion of the methanol-containing stream to the FCC reaction that is necessary to establish equilibrium conditions with the nitrile concentration entering the MTBE reaction zone in the FCC effluent.

The method used for monitoring the nitrile concentration in the methanol-containing stream that is recycled to the MTBE reaction zone can be any such method known to those skilled in the art. It is preferred that the method of monitoring the ACN concentration be capable of detecting nitrile concentrations as low as 1 mass ppm. A suitable method would be introducing a predetermined sample volume of the methanol-containing stream into a gas chromatograph that is equipped with a megabore fused silica capillary column that is internally coated with polyethylene glycol and a flame ionization detector.

As previously stated, an essential feature of the present invention is passing at least a portion of the methanol-containing stream that is normally recycled to the MTBE reactor to the FCC reaction zone. Any FCC process known to those skilled in the art is suitable for use in the present invention. In a preferred embodiment, the reactor section of the FCC unit includes the features of dilute phase cracking in the riser and quick-quench cracking. Additional information regarding FCC unit process conditions and features suitable for use in the present invention can be found in Meyers, Robert A., *Handbook of Petroleum Refining Processes*, McGraw Hill, Inc. pages 2-9 to 2-32 (1986).

In the FCC process of the present invention, at least a portion of the methanol-containing stream is directed to the reactor section of the FCC unit and contacted with an FCC feedstock in the presence of a finely divided, regenerated catalyst. Suitable FCC feedstocks include, but are not limited to straight-run atmospheric gas oils, vacuum gas oils, and certain atmospheric residues. The FCC catalyst can be any FCC catalyst known to those skilled in the art, preferably a zeolite-containing catalyst.

Once separated from the reactor section of the FCC unit, the hydrocarbon product vapor stream is passed to a fractionation section. Gasoline and gaseous olefin-rich co-products are taken overhead and routed to a gas concentration unit. In the gas concentration unit, the olefin-rich gas is compressed and directed through a series of absorbers, strippers and fractionation towers to produce the FCC effluent of the present invention.

It is contemplated that nitrile removal from an FCC effluent stream used to feed an etherification unit can be reduced by passing at least a portion or, under some circumstances, substantially all of the methanol-containing stream to a disposal or consumption zone.

Referring to the figure, an FCC hydrocarbon gas oil feedstock enters an FCC section 6 at line 2. An FCC effluent stream exits the FCC section 6 via line 8. The FCC effluent stream comprises $C_4$ olefinic hydrocarbons, metal cations (such as sodium), nitrogen compounds such as ammonia and nitriles such as acetonitrile (ACN), and sulfur compounds such as $H_2S$, COS, and mercaptans.

The sulfur compounds are removed from the FCC effluent by passing the effluent to a sulfur treatment zone 10 via line 8. The sulfur treatment zone 10 consists of at least one amine treating unit for removing $H_2S$ and COS from the FCC effluent and at least one mercaptan treating unit for removing mercaptan compounds (both units not shown).

After desulfurizing the FCC effluent, the FCC effluent is passed via line 12 to a selective hydrogenation zone 13 to remove diolefins.

The FCC effluent exits the selective hydrogenation zone 13 by line 3 and enters the MTBE reaction zone 14. The MTBE reaction zone 14 contains at least one guard bed (not shown) for removing metal cations and basic nitrogenates and at least one adiabatic fixed-bed reactor (not shown). In the MTBE reaction zone 14, isobutylene contained in the FCC effluent is reacted with methanol (which enters the MTBE reaction section 14 at recycle stream 48) to form MTBE reaction products. Exiting the MTBE reactor 14 at line 16 is an MTBE effluent stream. The MTBE effluent stream comprises MTBE, side reaction products such as TBA and DME, unconverted reactants such as methanol and isobutylene, and ACN.

The MTBE effluent stream enters a reactive distillation column 22 at line 16. Disposed in the reactive-distillation column 22 is a sulfonic ion exchange resin catalyst that is integrally combined with packing material to form a dual function reaction and mass transfer material 21. In the reactive distillation column 22, the methanol and remaining $C_4$ hydrocarbons further react to form additional MTBE, while at the same time MTBE reaction products are continuously separated from the unconverted reactants. Accordingly, an overhead raffinate stream 20 comprising unconverted methanol and $C_4$ hydrocarbons, undesirable side reaction products (such as TBA and DME), and ACN exits the top of the reactive distillation column 22.

The next step is to recover the methanol for reuse in the MTBE reaction section 14 by passing the overhead raffinate stream via line 20 into a raffinate water wash zone 30. A water-containing stream enters the raffinate water wash zone 30 via line 32 and is countercurrently contacted with the overhead raffinate which enters the raffinate water wash zone at line 20. Exiting the top of the raffinate wash zone 30 at line 26 is a hydrocarbon-rich stream that contains unconverted $C_4$ hydrocarbons and side reaction products. Exiting the bottom of the raffinate water wash zone 30 by line 24 is a methanol-containing stream.

The methanol-containing stream enters a methanol fractionation zone 36 via line 24. It is in the methanol fractionation zone 36 that the methanol and water are separated. Water exits the column 36 by line 32 and is recycled to the raffinate water wash zone 30. A methanol-rich stream exits the fractionation zone 36 at line 34.

At least a portion of the methanol-rich stream is set aside at junction 38 and recycled by line 39 to the FCC reaction zone 6. The remainder of the methanol-rich stream is routed to the MTBE reaction zone 14. Fresh makeup methanol is added to the process at line 40.

EXAMPLES

Example 1 is illustrative of a flow scheme in which none of the methanol recycle stream from the MTBE reactor effluent fractionator was dragged to the FCC reactor, i.e., all of the methanol recycle stream was fed to the MTBE reactors. Example 2 is illustrative of a flow scheme in which all of the methanol recycle stream from the MTBE reactor effluent fractionator was dragged to the FCC reactor, i.e., none of the methanol recycle stream was fed the MTBE reactors.

EXAMPLE 1

Fresh isobutylene was fed along with a recycle methanol stream into two MTBE reactors in series. The fresh isobutylene was fed at a rate of 95549 lbs/hr and contained 30 ppm by weight of ACN. The recycle methanol stream was fed at a rate of 2278 lbs/hr and contained 5500 ppm by weight ACN. In addition, fresh methanol was added at a rate of 7227 lbs/hr and contained no ACN. Accordingly, the combined feed stream entering the MTBE reactors had a flow rate of 95549 lbs/hr and contained 158 ppm by weight ACN.

The effluent from the MTBE reactors was then sent to a fractionation tower where a raffinate stream containing unreacted reactants was withdrawn overhead and a product stream containing MTBE was withdrawn from the bottom of the fractionation tower.

Based on a lay down rate of 3 wt. %, the buildup of ACN on the MTBE ion exchange resin catalyst was 0.45 lbs/hr.

EXAMPLE 2

Fresh isobutylene was fed along with a fresh methanol stream into two MTBE reactors in series. The fresh isobutylene was fed at a rate of 95549 lbs/hr and contained 30 ppm by weight of ACN. A drag methanol stream was taken back to the FCC reactor at a rate of 2278 lbs/hr. This drag stream contained 5500 ppm by weight ACN. Fresh methanol was added to the MTBE reactor at a rate of 9505 lbs/hr and contained no ACN. Accordingly, the combined feed stream entering the MTBE reactors had a flow rate of 95549 lbs/hr and contained 27 ppm by weight ACN.

The effluent from the MTBE reactors was then sent to a fractionation tower where a raffinate stream containing unreacted reactants was withdrawn overhead and a product stream containing MTBE was withdrawn from the bottom of the fractionation tower.

Based on a lay down rate of 3 wt. % the buildup of ACN on the MTBE ion exchange resin catalyst was 0.077 lbs/hr.

Accordingly, the expected MTBE ion exchange resin catalyst life improvement was about 5–6 times that of Example 1.

What is claimed:

1. A method of treating an effluent of a fluid catalytic cracking zone, said effluent comprising isoalkenes and at least one nitrile compound which method comprises the steps of:
    (a) contacting said effluent with a $C_1$–$C_5$ monohydroxy alcohol in the presence of an etherification catalyst in an etherification zone under etherification conditions to react said isoalkenes with said alcohol to produce an etherification effluent stream comprising an ether;
    (b) passing at least a portion of said etherification effluent stream to a separation zone to produce an ether-rich stream and a raffinate stream comprising said nitrile compound;
    (c) passing said raffinate stream to an alcohol recovery zone to produce a hydrocarbon-rich raffinate stream and an alcohol-containing stream;
    (d) recycling at least a portion of said alcohol-containing stream to said fluid catalytic cracking zone and
    (e) recycling any remainder of said alcohol-containing stream to etherification zone.

2. The method of claim 1 wherein said alcohol comprises methanol.

3. The method of claim 1 wherein said separation zone comprises a distillation zone.

4. The method of claim 3 wherein said distillation zone comprises a reactive distillation zone containing a bed of etherification catalyst to produce said ether.

5. The method of claim 1 wherein said ether comprises methyl tertiary butyl ether.

6. The method of claim 1 wherein said ether comprises tertiary amyl ether.

7. The method of claim 1 wherein said fluid catalytic cracking effluent is contacted with a selective hydrogenation catalyst at selective hydrogenation conditions in a selective hydrogenation zone to selectively saturate diolefins to monoolefins.

8. The method of claim 1 wherein said etherification catalyst comprises a macroporous acid-form sulfonic ion exchange resin.

9. The method of claim 1 further comprising treating said fluid catalytic cracking effluent to remove sulfur compounds prior to contacting said effluent with said alcohol.

10. The method of claim 1 further comprising monitoring the nitrile concentration of said alcohol-containing stream.

11. The method of claim 8 wherein said nitrile compound comprises acetonitrile.

12. The method of claim 1 further comprising fractionating said alcohol-containing stream to remove water prior to recycling said alcohol-containing stream to said fluid catalytic cracking zone.

13. A method of treating an effluent of a fluid catalytic cracking zone, said effluent comprising isobutene and at least one nitrile compound which method comprises the steps of:
    (a) contacting said effluent with methanol in the presence of an etherification catalyst in an etherification zone under etherification conditions to react said isobutene with said methanol to produce an etherification effluent stream which comprises methyl tertiary butyl ether;
    (b) passing at least a portion of said etherification effluent stream to a distillation zone containing an etherification catalyst and contacting said methanol in the presence of said etherification catalyst in said distillation zone at etherification conditions to produce a methyl tertiary butyl ether-rich stream and an overhead raffinate stream;
    (c) contacting said raffinate stream with a water-containing stream to produce a hydrocarbon-rich raffinate stream and a methanol-containing stream;
    (d) monitoring the nitrile concentration of said methanol-containing stream;
    (e) regulating said nitrile concentration in said methanol-containing stream by recycling at least a portion of said methanol-containing stream to said fluid catalytic cracking zone; and
    (f) recycling any remainder of said alcohol-containing stream to said etherification zone.

14. The method of claim 13 wherein said distillation zone comprises a reactive distillation zone containing a bed of etherification catalyst.

15. The method of claim 13 wherein said fluid catalytic cracking effluent is contacted with a selective hydrogenation catalyst at selective hydrogenation conditions in a selective hydrogenation zone to selectively saturate diolefins to monoolefins.

16. The method of claim 13 wherein said etherification catalyst comprises a macroporous acid-form sulfonic ion exchange resin.

17. The method of claim 13 further comprising treating said fluid catalytic cracking effluent to remove sulfur compounds prior to contacting said effluent with said methanol.

18. The method of claim 13 further comprising fractionating said methanol-containing stream to remove water prior to recycling said methanol-containing stream to said fluid catalytic cracking zone.

19. The method of claim 13 wherein said nitrile comprises acetonitrile.

20. A method for fluid catalytic cracking of a hydrocarbon feedstock which method comprises the steps of:
    (a) contacting said hydrocarbon feedstock with a fluid catalytic cracking catalyst in a fluid catalytic cracking zone under fluid catalytic cracking conditions to produce a fluid catalytic cracking effluent stream comprising isobutene;
    (b) treating said fluid catalytic cracking effluent stream to remove a substantial amount of any sulfur compounds contained therein;
    (c) contacting said effluent from step (b) with a selective hydrogenation catalyst at selective hydrogenation conditions in a selective hydrogenation zone to selectively saturate diolefins to monoolefins;
    (d) contacting said effluent from step (c) with methanol in the presence of an etherification catalyst comprising a macroporous acid-form sulfonic ion exchange resin in an etherification zone under etherification conditions to react said isobutene with said methanol to produce an etherification effluent stream which comprises methyl tertiary butyl ether;

(e) passing at least a portion of said etherification effluent stream to a distillation zone containing a bed of etherification catalyst comprising a macroporous acid-form sulfonic ion exchange resin and contacting said methanol in said bed of etherification catalyst in said distillation zone at etherification conditions to produce a methyl tertiary butyl ether-rich stream and an overhead raffinate stream comprising isobutane, normal butene, normal butane, methanol and isobutene;

(f) contacting said raffinate stream with a water-containing stream to produce a hydrocarbon-rich raffinate stream and a methanol-containing stream;

(g) fractionating said methanol-containing stream to produce a methanol-rich stream;

(h) monitoring acetonitrile concentration of said methanol-rich stream;

(i) regulating said acetonitrile concentration in said methanol-rich stream by recycling at least a portion of said methanol-rich stream to said fluid catalytic cracking zone; and (j) recycling any remainder of said alcohol-containing stream to said etherification zone.

* * * * *